(12) United States Patent
Kamkar et al.

(10) Patent No.: US 8,800,089 B2
(45) Date of Patent: Aug. 12, 2014

(54) PROCESS FOR CLEANING TEETH

(75) Inventors: Kirtan Shravan Kamkar, Bangalore (IN); Amit Sah, Bangalore (IN); Rudra Saurabh Shresth, Bangalore (IN); Narayanan Subrahmaniam, Bangalore (IN); Suresh Sambamurthy Jayaraman, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 297 days.

(21) Appl. No.: 13/390,430

(22) PCT Filed: Aug. 9, 2010

(86) PCT No.: PCT/EP2010/061552
§ 371 (c)(1),
(2), (4) Date: Feb. 14, 2012

(87) PCT Pub. No.: WO2011/020730
PCT Pub. Date: Feb. 24, 2011

(65) Prior Publication Data
US 2012/0225404 A1    Sep. 6, 2012

(30) Foreign Application Priority Data
Aug. 19, 2009   (IN) .................. 1901/MUM/2009

(51) Int. Cl.
*A46B 13/04* (2006.01)
*A61C 17/36* (2006.01)

(52) U.S. Cl.
USPC ................................. 15/29; 433/82

(58) Field of Classification Search
CPC ....... A46B 13/04; A61C 17/022; A61C 17/36
USPC ........................ 15/22.1, 29; 433/82
See application file for complete search history.

(56) References Cited

U.S. PATENT DOCUMENTS

| 3,021,702 A | 2/1962 | Houser |
| 3,108,465 A | 10/1963 | Bochan |

(Continued)

FOREIGN PATENT DOCUMENTS

| CH | 423720 A | 11/1966 |
| CH | 423720 | 11/1996 |

(Continued)

OTHER PUBLICATIONS

PCT International Search Report in PCT application PCT/EP2010/061552 dated Nov. 5, 2010 with Written Opinion.

(Continued)

*Primary Examiner* — Randall Chin
(74) *Attorney, Agent, or Firm* — Greenberg Traurig, LLP

(57) ABSTRACT

The present invention is in the field of tooth cleaning devices, especially electrical toothbrushes. The invention further relates to the use of an air/water jet for the cleaning of teeth. A process for cleaning teeth that incorporates a water jet for cleaning teeth remains to be desired, especially a single device that can be employed to clean teeth and reliably deposit material onto teeth. It is therefore an object of the present invention to provide a process for cleaning teeth with an electrical toothbrush device providing improved cleaning by means of an externally mixed air-water jet wherein the water dosing is not influenced by the air pressure. Surprisingly it has been found that a tooth brush device, comprising an air/water jet, wherein the air and water are mixed outside the nozzle(s), provides improved cleaning of dental surfaces, including inter-proximal areas, with low usage of water.

6 Claims, 3 Drawing Sheets

(56) References Cited

U.S. PATENT DOCUMENTS

| | | |
|---|---|---|
| 4,127,913 A | 12/1978 | Monson |
| 4,569,483 A | 2/1986 | Oberdorfer |
| 4,787,404 A | 11/1988 | Klosterman |
| 4,793,332 A | 12/1988 | Klein |
| 4,998,993 A | 3/1991 | Kenderi |
| 5,001,806 A | 3/1991 | Gurstein |
| 5,505,915 A | 4/1996 | Copeland |
| 5,593,304 A | 1/1997 | Ram |
| 5,820,373 A | 10/1998 | Okano |
| 5,930,858 A | 8/1999 | Jung |
| 5,943,723 A | 8/1999 | Hilfinger |
| 5,960,503 A | 10/1999 | Del Pozo |
| 5,974,615 A | 11/1999 | Schwarz-Hartmann |
| 6,264,119 B1 * | 7/2001 | Truong .................. 239/310 |
| 6,386,466 B1 | 5/2002 | Ozawa |
| 6,457,974 B1 | 10/2002 | Sharp et al. |
| 7,021,571 B1 | 4/2006 | Lawson |
| 8,016,949 B2 | 9/2011 | Jayaraman |
| 2002/0059947 A1 | 5/2002 | Sato |
| 2002/0189641 A1 | 12/2002 | Sato |
| 2003/0205631 A1 | 11/2003 | Barron |
| 2004/0087158 A1 | 5/2004 | Izumi |
| 2006/0078844 A1 * | 4/2006 | Goldman et al. ............... 433/80 |
| 2008/0135639 A1 | 6/2008 | Winters |
| 2008/0295864 A1 | 12/2008 | Turner |

FOREIGN PATENT DOCUMENTS

| | | |
|---|---|---|
| DE | 202005019242 U | 8/2006 |
| DE | 202005019242 U1 | 8/2006 |
| EP | 0140505 A1 | 5/1985 |
| EP | 0248638 A2 | 12/1987 |
| EP | 0790809 B1 | 12/1998 |
| EP | 0862390 B1 | 9/1999 |
| EP | 1250959 A1 | 10/2002 |
| EP | 1306136 A1 | 5/2003 |
| EP | 1737025 A1 | 12/2006 |
| EP | 1870381 A1 | 12/2007 |
| FR | 1014273 | 8/1952 |
| FR | 1094132 | 5/1955 |
| FR | 1108989 | 1/1956 |
| FR | 1281617 | 1/1962 |
| FR | 2 583 630 | * 12/1986 |
| FR | 2583630 | 12/1986 |
| FR | 2583630 A1 | 12/1986 |
| GB | 1049162 | 11/1966 |
| JP | 03296475 A | 12/1991 |
| JP | 2000317412 | 11/2000 |
| JP | 2001321391 | 11/2001 |
| WO | WO8403237 A1 | 8/1984 |
| WO | WO9936499 | 7/1999 |
| WO | WO02072274 A1 | 9/2002 |
| WO | WO03102289 A1 | 12/2003 |
| WO | WO2006041920 A1 | 4/2006 |
| WO | WO2008155025 A1 | 12/2008 |
| WO | WO2009103595 A1 | 8/2009 |
| WO | WO2011020730 A1 | 2/2011 |
| WO | WO2011020731 A3 | 2/2011 |
| WO | WO2011020733 A3 | 2/2011 |
| WO | WO2011020734 A2 | 2/2011 |

OTHER PUBLICATIONS

European Search Report in EP application EP 09 17 3652 dated Apr. 30, 2010.

PCT International Search Report in PCT application PCT/EP2010/061554 dated Apr. 14, 2011 with Written Opinion.

European Search Report in EP application EP 09 17 3657 dated Apr. 30, 2012.

PCT Internationational Search Report in PCT application PCT/EP2010/061556 dated Apr. 14, 2012 with Written Opinion.

European Search Report in EP application EP 09 17 3659 dated Feb. 11, 2010.

PCT International Search Report in PCT application PCT/EP2010/061557 dated Apr. 14, 2011 with Written Opinion.

European Search Report in EP application EP 09 17 3663 dated Nov. 30, 2009.

* cited by examiner

Top View

Side View

PROCESS FOR CLEANING TEETH

TECHNICAL FIELD

The present invention is in the field of tooth cleaning devices, especially electrical toothbrushes. The invention further relates to the use of an air/water jet for the cleaning of teeth.

BACKGROUND AND PRIOR ART

Toothbrushes and the practice of brushing teeth are widely spread throughout the world. In the last decades, the use of electrical toothbrushes has become more and more common, especially in the developed world.

Electrical toothbrushes come in many shapes and forms, but are mostly based on the same principle of a motor operating the movement of a shaft in at least one direction. Such electric toothbrushes are disclosed in e.g. U.S. Pat. No. 5,974,615, EP-A1-0 790 809 or EP-A1-0 862 390.

Mouth showers or mouth wash devices are also known in the art. Mouth wash devices have been commonly used in since the late 1970'ies and early 1980'ies. An example of such devices is found in U.S. Pat. No. 4,793,332, wherein the use of a multi jet spray mouth wash device is disclosed.

Some attempts have been made to integrate the two into a device that includes both a brushing part and a water jet. WO2006/041920 discloses an electrical toothbrush device comprising a water jet nozzle. However, this design uses an internal mix of air and water, resulting in unreliable water flow rates, or the need of a complex water pump.

Additionally, some toothbrushes have been disclosed (e.g. in WO2008/155025), wherein the brush head comprises an outlet or channel to dispense toothpaste.

Internally mixed air water jet for cleaning tooth is also known in the art. U.S. Pat. No. 5,820,373 discloses a periodontal pocket cleaning device for the prevention of periodontal disease, which is least liable to cause injury to the periodontal pocket, which can be used at any place without limiting the place of its use, which is able to obtain a stabilized atomized jet without being influenced by the height position of the handy probe, and which is available at a low cost. Also U.S. Pat. No. 5,593,304 discloses a dental apparatus includes a handpiece graspable at one end by a user, and a head at the opposite end of the handpiece including a single nozzle, or a pair of nozzles connectible to a source of liquid, a gas, and/or powder.

One of the problems encountered when integrating a mouth wash device with a toothbrush is that the mouth wash devices are intended to rinse the mouth, rather than for active cleaning, and therefore do not provide suitable cleaning.

Another problem is that while, water is appreciated for washing or rinsing the mouth it is not very convenient when brushing teeth, as toothpaste is then flushed away and while the accumulation of water in the mouth is not generally appreciated by the consumer.

The problem associated with internally mixed air water jet is that the cleaning performance is not up to the mark and the liquid flow is affected by the air-pressure due to the non-separation of the air and water nozzles opening which is not desirable.

A process for cleaning teeth using a device that incorporates a water jet for cleaning teeth remains to be desired, especially a single device that can be employed to clean teeth and reliably deposit material onto teeth.

It is therefore an object of the present invention to provide a process for cleaning tooth with an electrical toothbrush device providing improved cleaning by means of an externally mixed air-water jet wherein the water dosing is not influenced by the air pressure.

It is a further object to provide such improved cleaning while avoiding the use of a large volume of water.

It is a further object of the invention to provide improved removal of plaque, particles, and colour from teeth; especially from the inter-proximal areas of teeth.

It is yet a further object to provide a process for cleaning teeth using a device that can reliably deliver a predetermined amount of liquid, preferably comprising a benefit agent.

There are many methods that have been reported for cleaning dental surfaces, for instance mechanical/physical methods like scrubbing, buffing, abrasion, ultrasonication or use of chemical methods such as use of surfactants, solvents, acids, alkalis, bleaches and enzymes, for instance included in a toothpaste formulation.

In our co-pending application PCT/EP2009/050869 (published as WO2009/103595), a cleaning device is disclosed that comprises a novel kind of air/water jet and methods for using the same for cleaning substrates, such as fabric articles.

Surprisingly it has been found that a tooth brush device, comprising an air/water jet, wherein the air and water are mixed outside the nozzle(s), provides improved cleaning of dental surfaces, including inter-proximal areas, with low usage of water.

SUMMARY OF THE INVENTION

Accordingly, the present invention provides a process for cleaning teeth with a tooth cleaning device comprising an air-water jet device comprising two nozzles, wherein a first nozzle is in fluid communication with a feed liquid source; and a second nozzle connected to a source of compressed air; and characterised in that both nozzles are positioned relative to a central axis, wherein the first nozzle is at an angle of between 1 and 60° relative to the central axis; and the second nozzle is at an angle of between 1 and 45° relative to the central axis, wherein the air nozzle is not co-axially surround the water passage and wherein the mouth of the second nozzle is positioned more forward in the direction of the flow along the direction of the central axis than the mouth of the first nozzle, wherein the offset distance between the mouth of the first nozzle and the second nozzle is between 0.5 and 5 mm in said direction.

In another aspect the invention provides a process for cleaning teeth with a cleaning system comprising the tooth cleaning device according to the invention and a mouth-wash composition as feed liquid source.

These and other aspects, features and advantages will become apparent to those of ordinary skill in the art from a reading of the following detailed description and the appended claims. For the avoidance of doubt, any feature of one aspect of the present invention may be utilised in any other aspect of the invention. It is noted that the examples given in the description below are intended to clarify the invention and are not intended to limit the invention to those examples per se. Similarly, all percentages are weight/weight percentages unless otherwise indicated. Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention thus relates to a process for cleaning teeth comprising an air-water jet. It is preferred that the air-water jet of the invention is incorporated in a toothbrush, wherein the nozzles are positioned into the brush head, while at least part of the peripheral part may be incorporated in the handle.

Air-Water Jet

The air-water jet device comprises two nozzles wherein a first nozzle is in fluid communication with a feed liquid source; and a second nozzle connected to a source of compressed air.

The liquid source may be any water source, either provided to the air-water jet device straight from the water mains, through a pump, through a pressured container holding the water or by any other means, or even by gravity (i.e. by placing the water reservoir above the height of use of the air-water jet.

The feed liquid may be any liquid, but is preferably water, and aqueous solution or a mouth wash composition. The nozzle for the liquid is called water nozzle herein below, but it is understood that the water nozzle may pass water or any other liquid, including aqueous liquids and mouthwash compositions.

Similarly, the air source may be any air source, either provided through a compressor, separate from, or built into the tooth cleaning device, or through a compressed air line, such as often available in hospitals and in dental clinics.

Both, the first nozzle, (water nozzle) and the second nozzle (air nozzle) are positioned relative to an imaginary central axis (NOR). The first nozzle is positioned at an angle ($\alpha$) of between 1 and 60°, preferably between 10° and 30° relative to the central axis; and the second nozzle is at an angle ($\phi$) of between 1 and 45°, preferably between 15° and 30° relative to the central axis.

The mouth of the second nozzle is positioned more forward in the direction of the flow along the direction of the central axis than the mouth of the first nozzle, wherein the offset (OS) distance between the mouth of the first nozzle and the second nozzle is between 0.5 and 5 mm in said direction, preferably 1-3 mm.

The best results are obtained when the first nozzle has an opening of between 0.05 and 10 mm$^2$, preferably even at least 0.2 mm$^2$, and not more than 7 mm$^2$, more preferably not more than 5 mm$^2$ or even less than and 3 mm$^2$. Similarly, the opening of the second nozzle is preferably between 0.2 and 3 mm$^2$.

The scope of the present invention further includes configurations comprising two or more water nozzles directed at a single air nozzle. Although this adds to the complexity of the device, which is generally not preferred, it provides the additional benefit of point of action mixing or reacting different or incompatible ingredients.

For nozzles with a circular opening, the diameter of the first nozzle is preferably between 0.25 and 3.5 mm, preferably at least 0.5 mm, but preferably not more than 3 mm, more preferably not more than 2.5 mm, or even less than 3 mm; while the diameter of the second nozzle is preferably between 0.5 and 2 mm.

Without wishing to be bound by a theory, it is thought that the present invention derives its performance from the positioning of the nozzles relative to the imaginary axis and the offset of the water nozzle (first nozzle) relative to the air nozzle (second nozzle). Because of this positioning, the feed liquid coming from the water nozzle forms a film around the air nozzle, and because of this, it gives a finer spray at a lower liquid-to-air ratio (i.e. using less liquid). The air flow from the air nozzle is thought to create a local under-pressure that ensures that the liquid is driven in the direction of the air nozzle along the air nozzle tip, regardless of in which direction the nozzle is pointed. Furthermore, the liquid flow is not affected by the air pressure due to the separation of the air and water nozzle openings, which is a common problem with internal mix nozzle designs.

It is therefore preferred that the liquid:air ratio is between 10:90 and 1:9999, more preferably less than 5:95, still more preferably less than 4:96, even more preferably less than 3:97, less than 2:98 or even less than 1:99, while the ratio is preferably higher than 3:9997, more preferably higher than 5:9995.

It is further preferred that there is only a short distance between the opening of the water nozzle and the side of the air nozzle, this distance is preferably less than 2 mm, more preferably less than 1 mm, or even less than 0.5 mm. It is most preferred that the opening of the water nozzle is touching the air nozzle.

It is preferred that the air nozzle does not co-axially surround the water passage. It is also preferred that the water nozzle does not co-axially surround the air nozzle.

The air pressure of the air source is preferably in the range of 1 to 5 bar. The air preferably has a velocity of greater than 80 m/s at the exit of the nozzle (the nozzle opening), preferably greater than 120 m/s, more preferably greater than 180 m/s, and most preferably greater than 250 m/s. Although the invention would work up to very high air velocities, it is preferred for constructional reasons and convenience for the user, that the air velocity is less than the speed of sound (i.e. less than 334 m/s). Depending on the nozzle diameter, the airflow rate is preferably between 3 and 50 l/min, preferably more than 5 l/min or even more than 10 l/min. The air flow rate is preferably less than 40 l/min, more preferably less than 30 l/min or even less than 25 l/min.

The liquid flow rate is typically between 2 and 100 ml/min, preferably more than 5 ml/min or even more than 10 ml/min, while the liquid flow rate is preferably less than 80 ml/min, more preferably less than 50 ml/min, or even less than 40 ml/min.

Configuration

The air and/or liquid sources may be incorporated into the device, or be fitted in a separate unit. In the latter case, a separate unit comprising a compressor, a compressed air cartridge or cylinder, or another source of air and/or a liquid reservoir, optionally connected to the water mains, is provided. The unit is connected to a hand held device by means of a tubing as air line and/or water line.

Brush Head

The tooth cleaning device preferably comprises a brush head and a handle. The brush head comprises the air-water jet device. The use of more than one air-water jet devices is also contemplated.

The tooth cleaning device of the present invention may further incorporate other tooth cleaning features such as bristles, gum massaging elements and/or tongue cleaning elements. These elements are preferably positioned in the brush head.

The brush head may further be electrically operated. In this respect, the brush head may be driven by an electric motor incorporated into the handle of the device. The motor may move the head back and forth linearly in the direction of the handle, back and forth transverse at a 90° angle with said direction, back and forth over an angle of 1-180°, preferably 1-90° or even 1-45° around an axis in the direction of the handle, in a circular motion around an axis transverse to the direction of the handle, or back and forth over an angle of 1-180°, preferably 1-90° or even 1-45° around an axis transverse to the direction of the handle; or a combination thereof. In all the above configurations, the air-water jet and the optional bristles and or gum massaging elements are preferably pointing in a direction that is transverse to the handle of the tooth cleaning device, while the optional tongue cleaning elements preferably point in the opposite direction.

The tooth cleaning device may further comprise an air compressor as air source. The compressor may be built into the handle of the device, or provided as a separate device that is connected to the air-water jet by means of a tube. The compressor, preferably provides at least 1 bar pressure and not more than 5 bar, preferably less than 4 bar. Thus, very low power compressors, typically in the range of 0.05 to 1 HP, can be used to achieve the above specifications. Due to a pressure drop in the tubing and the device, the pressure at the air nozzle will preferably be in the range of 1 to 4 bar, more preferably 2 to 3 bar. A device with a means to set the pressure is also contemplated; in this case the user is, for instance, able to choose between soft, medium and hard cleaning, similar to currently available standard toothbrushes which also come in these variants.

The liquid source may be the water mains, i.e. directly connected to the faucet, or be in the form of a separate reservoir. The pressure on the liquid source for use with the tooth cleaning device may be relatively low, preferably at least 0.05 bar, more preferably at least 0.1 bar, but preferably not more than 3 bar, more preferably less than 2.5 bar, still more preferably less than 2 bar.

When a separate reservoir is used as liquid source, said reservoir may be filled with water only, or a mouth wash composition.

The liquid reservoir may be placed above the level of use of the tooth cleaning device, such as to provide pressure, or may be pressured separately. When pressured separately, it is especially preferred that the reservoir is pressurised with compressed air from the compressed air source.

Liquid Mouth Wash Composition

Liquid mouth wash typically comprise a liquid continuous phase and one or more benefit agents. Most typically, the liquid continuous phase comprises water, usually as the major component, making up greater than 50%, or even greater than 90%, by weight of the feed liquid.

Such benefit agents may aid the removal of plaque or tartar. Alternatively, they may reduce gingivitis and/or caries control. In other cases, the liquid may be formulated to provide freshness of breath, flavour, or fragrance. Typically components in the feed liquid include a freshening agent; a surfactant, such sodium lauryl sulphate; an antibacterial agent; a tooth bleaching agent; a humectant, such as sorbitol; and/or a fluoride salt.

Some examples of antibacterial agents that may be employed in feed liquid are ingredients like phenols (e.g. triclosan), thymol, salol, tannic acid, hexachloraphene, chlorinated thymols, and quaternary ammonium compounds. Alcohols may also be included. Alcohols can help to solubilise components and can also help in reducing bacterial activity. Antibacterial agents are preferably present in the composition in a concentration of between 0.001 and 1% w. The antibacterial agent is preferably present at a concentration of at least 0.005% w, more preferably at least 0.01% w. The antibacterial agent is preferably present at a concentration of not more than 0.5% w, more preferably not more than 0.25% w, still more preferably less than 0.1%.

Fluoride salts, such as sodium fluoride or sodium monofluorophosphate are preferred components in the feed liquid. Fluoride is preferably present in the feed liquid in a concentration of between 4.5 and 4500 ppm of fluoride ion.

Fluoride is preferably present in the composition in a concentration of between 4.5 and 4500 ppm of fluoride. Fluoride is preferably present in the composition at a concentration of more than 23 ppm, more preferably more than 45 ppm and most preferably more than 113 ppm of fluoride. Fluoride is preferably present at a concentration of less than 2260 ppm, more preferably less than 1130 ppm or even less than 450 ppm of fluoride.

When sodium fluoride is used, it is preferably present in a concentration of between 0.005 and 0.5% (equivalent to between 23 and 2260 ppm of fluoride)

Other ingredients that may be included in the mouth wash composition are antifoaming agents, preservatives, colorants, and sweeteners.

Typical flavours that could be used are peppermint, menthol, methyl salicylate, eugenol, eucalyptol and/or mixtures thereof. Flavours are generally present in a concentration of between 0.001 and 1% w, preferably more than 0.01% w, even more than 0.05% w. The flavours are preferably present at a concentration of less than 0.5% w, even less than 0.25% w.

The compositions may comprise up to 35% by volume of ethanol, typically between 5 and 30% by volume, or even between 15 and 25% by volume.

The composition may also comprise a preservative. The preservative is typically present at a concentration of between 0.001 and 1%.

The mouthwash composition may optionally comprise an abrasive particle, such as calcite. The abrasive particle is preferably present in the composition in a concentration of between 0.1 and 10%. It is preferred that the particles are smaller than the mouth of the water nozzle, preferably the maximum particle size is less than 500 micrometer. The average particle size may be between 1 and 250 micrometer, more preferably between 10 and 200 micrometer, still more preferably between 5 and 150 micrometer.

Operation

While cleaning teeth ("brushing"), the air-water jet may be used continuously, or discontinuously. One way of operation that is considered is to use the air-water jet during part of the brushing. In another embodiment, the air-water jet is used in the first part of the brushing process for cleaning and run with only the liquid flow or the liquid flow and low air flow to deposit a benefit agent to the teeth. A preferred benefit agent is fluoride. In another embodiment the air-water jet is operated in a pulsed mode i.e. the air flow is controlled in an on-off fashion over time. In yet another embodiment the handheld device is fitted with a push button to switch the air-water jet on or off while brushing.

In any of the discontinuous operations, it is preferred to open and shut the air and/or liquid lines with a suitable solenoid valve.

A valve system may also be used to open the liquid and/or air lines when the device is in operation, while shutting the liquid and/or air lines when the device is not in use.

The invention will now be illustrated with reference to the following non-limiting figures and examples. The embodiments and examples are by way of illustration only and do not limit the scope of invention in any manner.

DETAILED DESCRIPTION OF THE DRAWINGS

Figure 1:
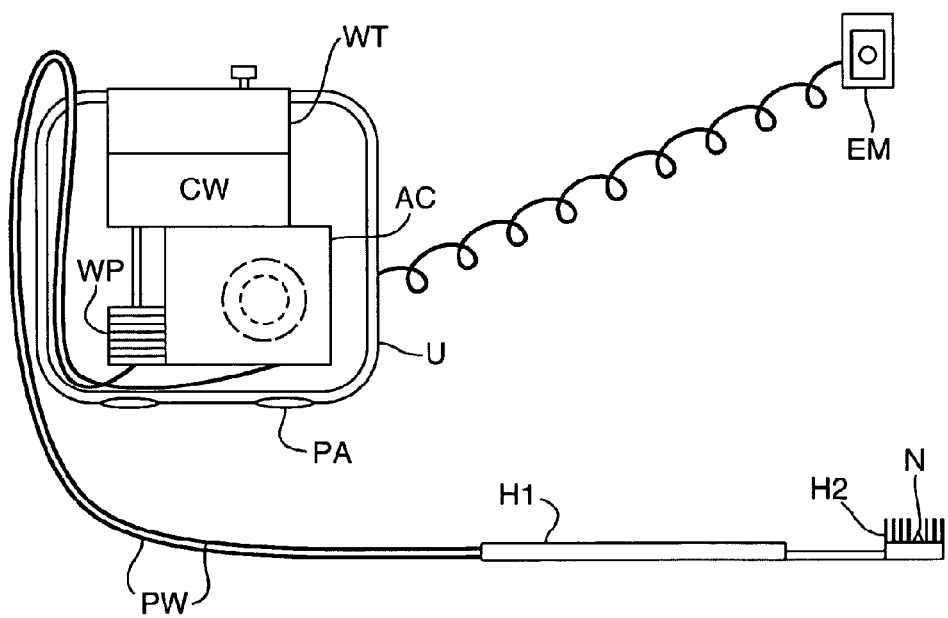
FIG. 1 is a schematic of a hand held embodiment of the device of the invention

Referring to FIG. 1, the device of the invention is embodied as a hand held device for cleaning fabric and shows the main unit (U) connected to the hand held device, which consists of a handle (H1) and a Head (H2). The device comprises an air compressor (AC) which weighs about 3 kg and runs on a motor that is rated at 130 W. The compressor is therefore light and easy to carry around like a household iron box for ironing clothes. The air compressor (AC) runs on electric power either from an electricity mains wall outlet (EM) or from a set of batteries. A container for liquid (CW) is provided for feeding the liquid or surfactant solution to the device. The liquid is fed to the nozzle (N) through a tube (PW) from the water pump (WP). Another tube (PA) feeds the compressed air from the air compressor (AC) to the nozzle (N). Air pressures of the order of 1 to 5 bar can be generated using this embodiment of the invention. The nozzle (N) is an external mix nozzle as is evident from FIG. 1.

Figure 2:
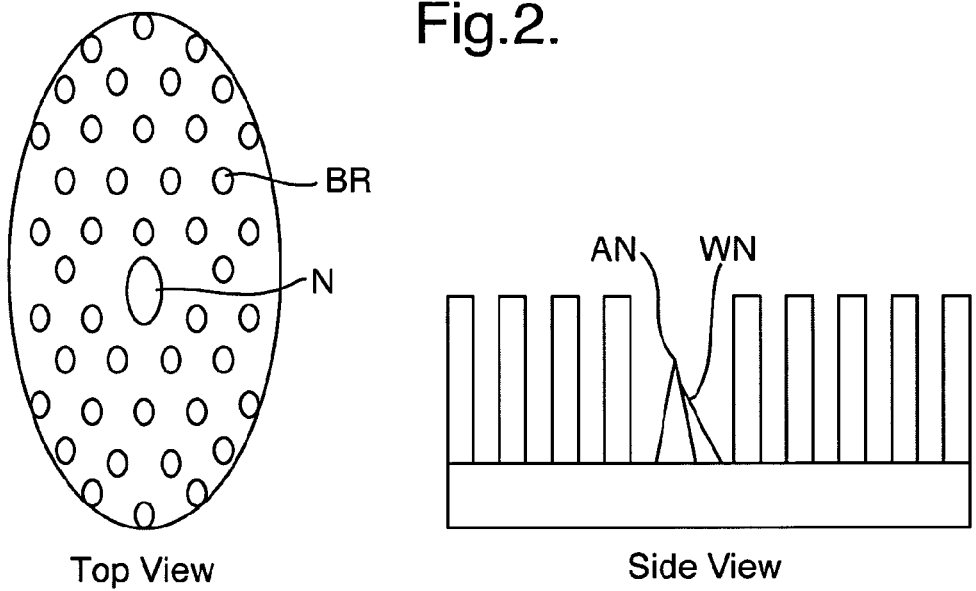
FIG. 2 is a schematic of a blown up view of the brush head

FIG. 2 shows a brush head comprising the air-water jet comprising two nozzles (N), one for air (AN) and one for water (WN) and bristles (BR). The nozzle is an external mix nozzle with an off-set.

Figure 3:
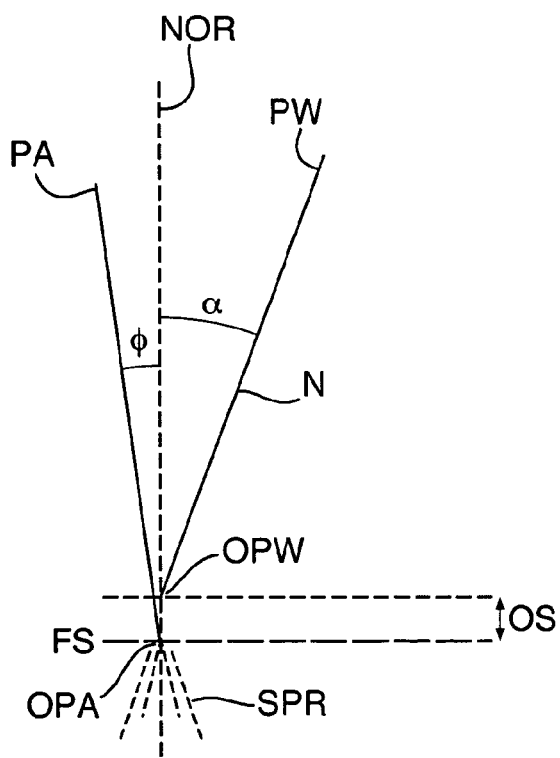
FIG. 3 is a detailed drawing of nozzles

Referring to FIG. 3, the nozzle (N) has the outlet port for liquid (OPW) positioned away from the substrate relative to the outlet port for air (OPA), offset by a distance (OS). The angle of incidence of the outlet port for liquid with respect to the substrate (FS) is defined by the angle $\alpha$. The angle of incidence of the outlet port for air with respect to the substrate (FS) is defined by the angle $\phi$. The dashed line NOR represents an imaginary line which is normal to the surface of the substrate. As is apparent, in this embodiment of the nozzle the angle $\alpha$ is greater than the angle $\phi$. The air exits from the nozzle through outlet port for air (OPA) and the liquid exits through the outlet port for liquid (OPW).

When in use, a liquid (e.g. water or a mouth wash solution) is fed to the container for liquid (CW). The power to the air compressor is switched on thereby generating air pressure in the air compressor. Compressed air is fed through tube (PA) while liquid or surfactant solution is fed through tube (PW). The air and liquid mix outside the nozzle creating a spray (SPR), which is used to clean teeth.

Figure 4:
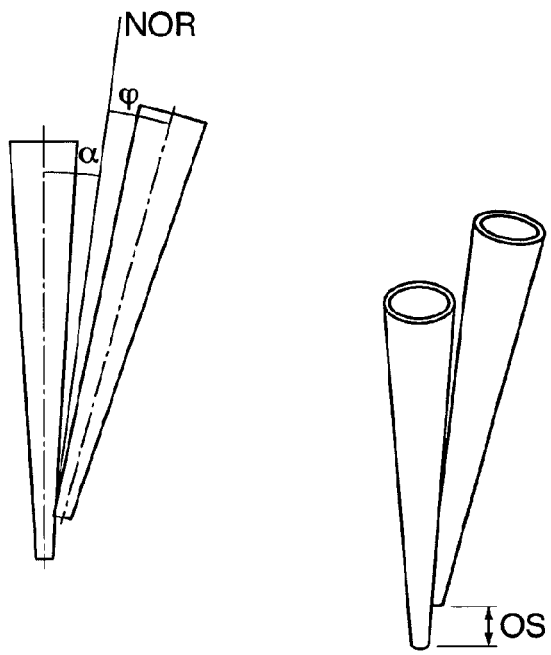
FIGS. 4 and 5 show 3-D drawings of the air-water jet nozzles in different embodiments.

FIG. 4 shows a 3-D view of the configuration of FIG. 3

Figure 5:
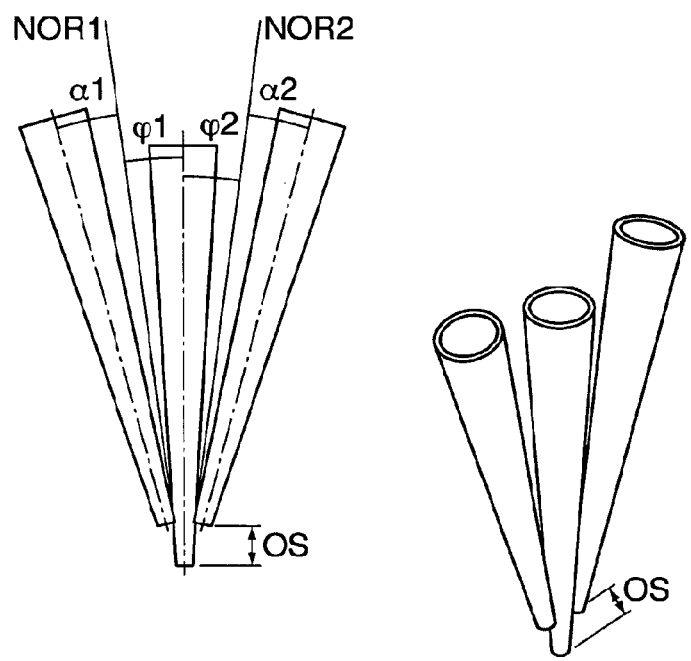

FIG. 5 shows a 3-D view of a configuration with 1 air nozzle and 2 water nozzles.

EXAMPLES

The invention will now be demonstrated with examples.

Example 1

Cleaning of Dentures

Artificial plaque was prepared by mixing paraffin wax, stearic acid and chalk. Details of preparation are as follows
Ingredients:—
Precipitated chalk—55 g
Liquid paraffin—40 g
Stearic acid—0.6 g
Method:
1) Take 40 g of liquid paraffin in 250 ml beaker
2) Add 0.6 g of stearic acid slowly.
3) Keep it on low hot plate/heater so as to make it dissolve.
4) Cool the solution to room temperature.
5) Slowly add this solution into mortar
6) Add precipitated chalk slowly to this solution in a mortar & stir to ensure good pasty material. Ensure addition/quantity and quality of grounding is such that no lumps are found.

Artificial plaque prepared by the above method was applied on model dentures including interstitials and gum lines. The cleaning efficiency of the present invention was compared against a conventional brush. In this example the air-water jet of the invention was built into the brush head of an Oral-B, model cross-action, electric toothbrush. For clarity, only the brush head was used, the electric motor and motion of the head were not used. In the comparative example the Oral-B, model cross-action, brush was used in the OFF position. The following experimental conditions were maintained:
Air pressure: 4 bar gauge
Water flow rate: 30 ml/min
Time of cleaning: 30 seconds To quantify the cleaning efficiency the dentures cleaned with air jet and brush were exposed to panel members. A score of zero was assigned to dentures completely covered with plaque and a score of ten was assigned to clean dentures. Average panel scores (averaged from scores from ten panel members) for cleaning with the air-water jet vs conventional brushing is presented below.

TABLE 1

Cleaning score with air jet vs conventional brush

|  | Average score on | Standard Deviation |
| --- | --- | --- |
| Air-water Jet | 8.4 | 0.5 |
| Regular Brush | 4.1 | 1.14 |

Data in Table 1 clearly shows that cleaning with air jet is significantly superior to conventional brushing.

Example 2

Removal Efficiency with Off-Set Vs without Off-Set

Protocol:
Artificial dentures were deposited with model plaque as explained in example 1. This was followed by cleaning with air jet for 30 seconds. The air pressure was 1.5 bar. One half of the denture was cleaned with a nozzle with an offset (3 mm) and the other half with a nozzle without offset. This experiment was repeated. The cleaned denture was shown to a panel for evaluation.
Set 1
Out of 13 people, 8 people picked the side cleaned with nozzles with an offset, 2 people picked the side with nozzles without offset and 3 picked no difference.
Set 2
Out of 10 people, 8 people picked the side of nozzle with an offset and 2 people picked up no differences.

From the data it is clear that the offset provides superior spray characteristics and consequently provides superior cleaning.

Example 3

Internal Mix Vs External Mix

One of the important features of the external mix design is that the liquid flow rate is independent of air pressure. This is important as the liquid flow rate is related to dosage of ingredients like fluoride and antimicrobial. A constant liquid flow rate, independent of air pressure, implies a constant dosage. On the other hand, with internal mix design the liquid flow rate is a strong function of air pressure for a given setting of pump. Table shows the liquid flow rate as a function of air pressure. From the table, it is clear that liquid flow rate decreases with an increase in air pressure.

TABLE 2

Water flow rate as a function of air pressure in internal mix

| Pressure (kg/cm$^2$) | Flow rate (ml/min.) Internal mix | Flow rate (ml/min.) External mix |
| --- | --- | --- |
| 1.25 | 14 | 14 |
| 1.50 | 8 | 14 |
| 1.75 | 4 | 14 |

With external mix, the water flow rate remained constant at 14 ml/min independent of the air pressure Example 4

Cleaning Data of the Device Relative to the Positioning of the Two Nozzles and Offset Between them The qualitative data to prove that offset between the nozzles responsible for better cleaning is already provided in Example 2.

The quantitative data to prove that offset provides better cleaning, experiments were done on a ceramic surface stained with model dental plaque as described above in example 1 with the air-water jet using only air and water and compared with the device that has no offset and a reversed offset. The results are scored on a 0-10 scale as indicated above in example 1.

The results of the experiment are tabulated below in Table 3:

TABLE 3

| Air outlet port | Water outlet port | Offset, mm | ΔR |
| --- | --- | --- | --- |
| Closer to substrate | Away from substrate | 5 | 6.8 |
| Away from substrate | Closer to substrate | 5 | 5.5 |
| Together with water outlet port | Together with air outlet port | — | 5.3 |

The data in Table 3 indicates that superior cleaning is obtained when the water nozzle is positioned at an offset relative to the air nozzle such that the water nozzle is further away from the substrate that the air nozzle as compared to when they are positioned together or at an offset in reversed order.

The invention claimed is:

1. A device comprising
   a. an air-water jet device configured to clean a dental surface comprising a first nozzle and a second nozzle;
   wherein:
      i. the first nozzle is in fluid communication with a feed liquid source;
      ii. the second nozzle is connected to a source of compressed air; and
      iii. both nozzles are positioned relative to a central axis, wherein the first nozzle is at an angle of between 1 and 60° relative to the central axis;
         wherein the second nozzle is at an angle of between 1 and 45° relative to the central axis; and
         wherein the central axis is normal to the dental surface;
   wherein a mouth of the second nozzle is positioned more forward in the direction of the flow along the direction of the central axis than a mouth of the first nozzle,
      wherein the offset distance between the mouth of the first nozzle and the second nozzle is between 0.5 and 5 mm in said direction;
   wherein the first nozzle and the second nozzle are positioned so as to result in:
      (i) mixing of the air and the feed liquid at the mouth of the second nozzle when the device is in operation and
      (ii) liquid from the first nozzle forming a film around the second nozzle when the device is in operation;
   wherein the second nozzle does not co-axially surround the first nozzle;
   wherein the distance between an opening of the first nozzle and a side of the second nozzle is less than 2 mm; and
   wherein the device further comprises a handle and a head, wherein the head further comprising bristles, and
      wherein the bristle-head is configured to be electrically operated.

2. A device according to claim 1, wherein the mouth of the first nozzle has an opening of 0.05-7 mm$^2$.

3. A device according to claim 2, wherein the mouth of the first nozzle has an opening of 0.2-3.5 mm$^2$.

4. A device according to claim 1, wherein the mouth of the first nozzle is less than 1 mm away from a wall of the second nozzle.

5. A device according to claim 1, further comprising a separate unit connected to the device;
   wherein the separate unit comprises a compressor and a reservoir;
      wherein the reservoir is configured to be the feed liquid source and
      wherein the compressor is configured to be the source of compressed air; and
   wherein the device is configured to be hand-held.

6. A device according to claim 1, wherein the feed liquid source comprises:
   a. 4.5 to 4500 ppm of fluoride
   b. 0.001 to 0.5% anti-bacterial agent
   c. 0 to 35% alcohol
   d. 0.001 to 1% flavour
   e. water.

* * * * *